(12) United States Patent
Kanehara et al.

(10) Patent No.: US 10,005,851 B2
(45) Date of Patent: Jun. 26, 2018

(54) POLYMERIZATION INITIATOR AND RADICALLY POLYMERIZABLE COMPOSITION CONTAINING SAME

(71) Applicant: ADEKA CORPORATION, Tokyo (JP)

(72) Inventors: Yukiko Kanehara, Tokyo (JP);
Tomoya Tamachi, Tokyo (JP);
Tomoyuki Ariyoshi, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days. days.

(21) Appl. No.: 15/318,780

(22) PCT Filed: Jul. 24, 2015

(86) PCT No.: PCT/JP2015/071077
§ 371 (c)(1),
(2) Date: Dec. 14, 2016

(87) PCT Pub. No.: WO2016/017537
PCT Pub. Date: Feb. 4, 2016

(65) Prior Publication Data
US 2017/0145121 A1    May 25, 2017

(30) Foreign Application Priority Data

Aug. 1, 2014  (JP) ................................. 2014-158115

(51) Int. Cl.
| | |
|---|---|
| *C08F 2/50* | (2006.01) |
| *C07D 295/10* | (2006.01) |
| *C07C 323/32* | (2006.01) |
| *C07F 7/18* | (2006.01) |
| *C07C 323/31* | (2006.01) |
| *C07D 295/116* | (2006.01) |
| *C08F 20/00* | (2006.01) |
| *C08F 2/38* | (2006.01) |

(52) U.S. Cl.
CPC .............. *C08F 2/50* (2013.01); *C07C 323/31* (2013.01); *C07C 323/32* (2013.01); *C07D 295/10* (2013.01); *C07D 295/116* (2013.01); *C07F 7/1836* (2013.01); *C08F 2/38* (2013.01); *C08F 20/00* (2013.01)

(58) Field of Classification Search
CPC ..... C08F 2/50; C07D 295/10; C07D 295/116; C07D 323/31; C07C 23/32; C07C 323/32; C07F 7/1836
See application file for complete search history.

(56) References Cited

U.S. PATENT DOCUMENTS

| | | | | |
|---|---|---|---|---|
| 4,284,485 A | * | 8/1981 | Berner ...................... | C08F 2/50 522/14 |
| 4,315,807 A | * | 2/1982 | Felder ................... | C07C 49/747 430/281.1 |
| 4,582,862 A | | 4/1986 | Berner et al. | |
| 4,977,151 A | | 12/1990 | Fujimori et al. | |
| 4,992,547 A | * | 2/1991 | Berner ...................... | C08F 2/50 522/101 |
| 5,077,402 A | * | 12/1991 | Desobry .............. | C07D 209/86 522/107 |
| 6,022,906 A | | 2/2000 | Ohwa et al. | |
| 6,057,380 A | * | 5/2000 | Birbaum ................. | G03F 7/038 430/280.1 |
| 6,204,306 B1 | * | 3/2001 | Chabrecek ............ | C07C 271/20 351/159.01 |
| 6,441,244 B1 | * | 8/2002 | Avar ....................... | C07C 45/46 544/106 |

(Continued)

FOREIGN PATENT DOCUMENTS

| | | |
|---|---|---|
| EP | 0306411 | 3/1989 |
| JP | 58-157805 | 9/1983 |

(Continued)

OTHER PUBLICATIONS

Ito Ryoichi; machine English translation of JP 63-070210 (Year: 1988).*
Shinano et al.; machine English translation of JP 2013-163670 (Year: 2013).*
International Search Report, PCT/JP2015/071077, dated Oct. 13, 2015.
Kastner, P . et al, Relationship between structure and reversed-phase thin-layer chromatographic lipophilicity parameters in a group of piperazine derivatives, Journal of Chromatography A, 1997, vol. 766, No. 1-2, p. 165-170.
Supplementary European Search Report dated Mar. 16, 2018 in corresponding European Patent Application No. 15827802.

*Primary Examiner* — Michael F Pepitone
*Assistant Examiner* — Jessica Marie Roswell
(74) *Attorney, Agent, or Firm* — Young & Thompson

(57) ABSTRACT

Provided is an α-aminoalkylphenone compound that has good stability and low sublimability, efficiently generates radicals when irradiated with a bright line at 365 nm (I line) or the like, and is useful as a polymerization initiator to be used in a radically polymerizable composition. The α-aminoalkylphenone compound is represented by Formula (I) mentioned below.

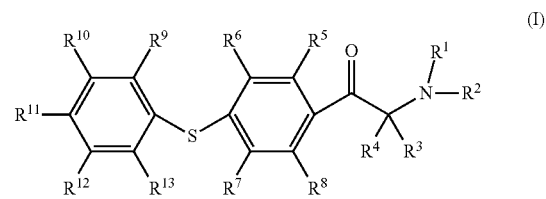

In Formula (I) mentioned above, it is preferable that $R^{11}$ is a nitro group, an alkoxy group having 1 to 12 carbon atoms, or an alkoxycarbonyl group having 1 to 12 carbon atoms. The α-aminoalkylphenone compound can be preferably used in a polymerization initiator.

5 Claims, No Drawings

(56) References Cited

U.S. PATENT DOCUMENTS 6,458,864 B1 * 10/2002 Asakura ................ A61K 6/083
 522/182
8,022,243 B1 * 9/2011 Chiu .................... C07C 323/32
 560/17

FOREIGN PATENT DOCUMENTS

| | | |
|---|---|---|
| JP | S63-070210 | 3/1988 |
| JP | 64-63574 | 3/1989 |
| JP | H10-069079 | 3/1998 |
| JP | 10-291969 | 11/1998 |
| JP | 2013-163670 | 8/2013 |

* cited by examiner

POLYMERIZATION INITIATOR AND RADICALLY POLYMERIZABLE COMPOSITION CONTAINING SAME

TECHNICAL FIELD

The present invention relates to a novel polymerization initiator having a diphenylsulfide skeleton and a radically polymerizable composition containing the polymerization initiator and a polymerizable compound having an ethylenically unsaturated bond.

BACKGROUND ART

Photosensitive compositions (radically polymerizable compositions) are obtained by adding a photopolymerization initiator to a polymerizable compound having an ethylenically unsaturated bond. The photosensitive compositions can be polymerized and cured by being irradiated with an energy beam (light) and are thus used in photosensitive printing plates, various photoresists, and the like.

With regard to a photopolymerization initiator to be used in the photosensitive compositions (radically polymerizable compositions), Patent Literature 1 discloses an optical fiber using an α-aminoalkylphenone derivative as the photopolymerization initiator, Patent Literature 2 discloses a photopolymerizable composition using an α-aminoalkylphenone derivative as the photopolymerization initiator, and Patent Literature 3 discloses a novel α-aminoacetophenone photoinitiator.

However, the α-aminoalkylphenone derivatives described in Patent Literatures 1 to 3 have insufficiently low sublimability and thus cause the contamination of a photomask and a heating furnace with sublimates, and the like.

CITATION LIST

Patent Literature

Patent Literature 1: JP S63-070210A
Patent Literature 2: JP H10-069079A
Patent Literature 3: U.S. Pat. No. 6,022,906(A)

SUMMARY OF INVENTION

A problem to be solved is that there have been no polymerization initiators that have satisfactory sensitivity.

Therefore, an object of the present invention is to provide a novel compound that has good stability and low sublimability, is activated by efficiently absorbing near-ultraviolet light at 365 nm or the like, and is useful as a highly sensitive polymerization initiator, a polymerization initiator using this compound, and a radically polymerizable composition.

The present invention achieves the object with providing an α-aminoalkylphenone compound represented by Formula (I) mentioned below:

Chemical Formula 1

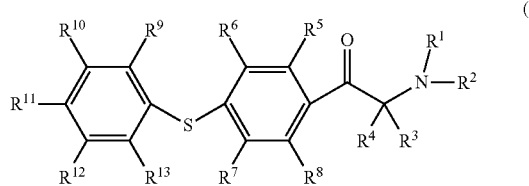

(I)

wherein $R^1$ and $R^2$ each independently represent a hydrogen atom; an alkyl group having 1 to 12 carbon atoms and optionally substituted with a hydroxyl group, a carboxyl group, a halogen atom, a cyano group, or a nitro group; a phenyl group optionally substituted with an alkyl group having 1 to 4 carbon atoms, a hydroxyl group, a carboxyl group, a halogen atom, a cyano group, or a nitro group; an arylalkyl group having 7 to 30 carbon atoms and optionally substituted with an alkyl group having 1 to 4 carbon atoms, a hydroxyl group, a carboxyl group, a halogen atom, a cyano group, or a nitro group; or an alkenyl group having 2 to 12 carbon atoms, and $R^1$ and $R^2$ optionally bind to each other to form a three- to six-membered heterocycle, $R^3$ and $R^4$ each independently represent a hydrogen atom; an alkyl group having 1 to 12 carbon atoms and optionally substituted with a hydroxyl group, a carboxyl group, a halogen atom, a cyano group, or a nitro group; a phenyl group optionally substituted with an alkyl group having 1 to 4 carbon atoms, a hydroxyl group, a carboxyl group, a halogen atom, a cyano group, or a nitro group; an arylalkyl group having 7 to 30 carbon atoms and optionally substituted with an alkyl group having 1 to 4 carbon atoms, a hydroxyl group, an alkoxy group having 1 to 4 carbon atoms, an amino group, an alkylthio group having 1 to 4 carbon atoms, a carboxyl group, a halogen atom, a cyano group, or a nitro group; or an alkenyl group having 2 to 12 carbon atoms, and $R^3$ and $R^4$ optionally bind to each other to form a three- to six-membered cycloalkane, $R^5$, $R^6$, $R^7$, and $R^8$ each independently represent a hydrogen atom, a halogen atom, a cyano group, a nitro group, a carboxyl group, or a hydroxyl group; an alkyl group having 1 to 8 carbon atoms and optionally substituted with a halogen atom; an arylalkyl group having 7 to 30 carbon atoms and optionally substituted with an alkyl group having 1 to 4 carbon atoms, a hydroxyl group, a carboxyl group, a halogen atom, a cyano group, or a nitro group, $R^9$, $R^{10}$, $R^{11}$, $R^{12}$, and $R^{13}$ each independently represent a hydrogen atom, a halogen atom, a cyano group, a nitro group, a carboxyl group, or a hydroxyl group; an alkyl group having 1 to 8 carbon atoms and optionally substituted with a halogen atom; an arylalkyl group having 7 to 30 carbon atoms and optionally substituted with an alkyl group having 1 to 4 carbon atoms, a hydroxyl group, a carboxyl group, a halogen atom, a cyano group, or a nitro group; or —$OR^{14}$, —O—CO—O—$R^{15}$, —$NR^{16}R^{17}$, or —$SR^{18}$, and at least one of $R^9$, $R^{10}$, $R^{11}$, $R^{12}$, and $R^{13}$ is a group selected from the group consisting of a nitro group, —$OR^{14}$, —O—CO—O—$R^{15}$, —$NR^{16}R^{17}$, and —$SR^{18}$, $R^{14}$, $R^{15}$, $R^{16}$, $R^{17}$, and $R^{18}$ represent an alkyl group having 1 to 12 carbon atoms and optionally substituted with a hydroxyl group, a carboxyl group, a halogen atom, a cyano group, or a nitro group; a phenyl group optionally substituted with a hydroxyl group, a carboxyl group, a halogen atom, a cyano group, or a nitro group; an arylalkyl group having 7 to 30 carbon atoms and optionally substituted with an alkyl group having 1 to 4 carbon atoms, a hydroxyl group, an alkoxy group having 1 to 4 carbon atoms, an amino group, an alkylthio group having 1 to 4 carbon atoms, a carboxyl group, a halogen atom, a cyano group, or a nitro group; an alkenyl group having 2 to 12 carbon atoms; or a heterocycle-containing group having 2 to 12 carbon atoms; a trialkylsilyl group; or a triaryl silyl group, a methylene chain in the alkyl group and the arylalkyl group is optionally replaced by —O—, —S—, —$NR^{19}$—, —CO—, —CO—O—, —O—CO—, or —O—CO—O—, and a terminus of the alkyl group optionally has an unsaturated bond, and $R^{19}$ represents a hydrogen atom; an alkyl group having 1 to 12 carbon atoms and optionally substituted with a hydroxyl group, a carboxyl group, a halogen atom, a cyano group, or a nitro group; a phenyl group optionally substituted with an alkyl group having 1 to 4 carbon atoms, a hydroxyl group, a carboxyl group, a halogen atom, a cyano group, or a nitro group; an arylalkyl group having 7 to 30 carbon atoms and optionally substituted with an alkyl group having 1 to 4 carbon atoms, a hydroxyl group, a carboxyl group, a halogen atom, a cyano group, or a nitro group; or an alkenyl group having 2 to 12 carbon atoms.

The present invention provides a radically polymerizable composition comprising a polymerization initiator (A) and a polymerizable compound having an ethylenically unsaturated bond (B), wherein the polymerization initiator (A) is the polymerization initiator according to the present invention.

The present invention provides a cured product obtained by irradiating the above-mentioned radically polymerizable composition with an energy beam.

DESCRIPTION OF EMBODIMENTS

Hereinafter, α-aminoalkylphenone compounds and polymerization initiators containing the compound according to the present invention will be described in detail based on preferred embodiments.

The α-aminoalkylphenone compounds according to the present invention are novel compounds represented by Formula (I) mentioned above.

Examples of the unsubstituted alkyl group having 1 to 12 carbon atoms represented by $R^1$, $R^2$, $R^3$, $R^4$, $R^{14}$, $R^{15}$, $R^{16}$, $R^{17}$, $R^{18}$, and $R^{19}$ in Formula (I) mentioned above include a methyl, an ethyl, a propyl, an isopropyl, a butyl, an isobutyl, an s-butyl, a t-butyl, an amyl, an isoamyl, a t-amyl, a hexyl, a heptyl, an octyl, an isooctyl, a 2-ethylhexyl, a t-octyl, a nonyl, an isononyl, a decyl, an isodecyl, an undecyl, a dodecyl, a tetradecyl, a hexadecyl, an octadecyl, an icosyl, a cyclopentyl, a cyclopentylmethyl, a cyclopentylethyl, a cyclohexyl, a cyclohexylmethyl, and a cyclohexylethyl.

Examples of the alkyl group having 1 to 12 carbon atoms, substituted with a hydroxyl group, a carboxyl group, a halogen atom, a cyano group, or a nitro group, represented by $R^1$, $R^2$, $R^3$, $R^4$, $R^{14}$, $R^{15}$, $R^{16}$, $R^{17}$, $R^{18}$, and $R^{19}$ in Formula (I) mentioned above, include the above-mentioned alkyl groups having 1 to 12 carbon atoms, which are partially or fully substituted with a hydroxyl group, a carboxyl group, a halogen atom, a cyano group, or a nitro group.

Examples of the unsubstituted alkyl group having 1 to 8 carbon atoms represented by $R^5$, $R^6$, $R^7$, $R^8$, $R^9$, $R^{10}$, $R^{11}$, $R^{12}$, and $R^{13}$ in Formula (I) mentioned above include the alkyl groups having 1 to 8 carbon atoms out of the above-mentioned examples of the unsubstituted alkyl groups having 1 to 12 carbon atoms.

Examples of the alkyl group having 1 to 8 carbon atoms, substituted with a halogen atom, and represented by $R^5$, $R^6$, $R^7$, $R^8$, $R^9$, $R^{10}$, $R^{11}$, $R^{12}$, and $R^{13}$ in Formula (I) mentioned above, include the above-mentioned alkyl groups having 1 to 8 carbon atoms, which are partially or fully substituted with a halogen atom.

Examples of the unsubstituted arylalkyl group having 7 to 30 carbon atoms represented by $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{19}$ in Formula (I) mentioned above include a benzyl, an α-methylbenzyl, an α,α-dimethylbenzyl, a phenylethyl, and a 9-fluorenylmethyl.

Examples of the arylalkyl group having 7 to 30 carbon atoms, substituted with an alkyl group having 1 to 4 carbon atoms, a hydroxyl group, a carboxyl group, a halogen atom, a cyano group, or a nitro group, and represented by $R^1$, $R^2$, $R^5$, $R^6$, $R^7$, $R^8$, $R^9$, $R^{10}$, $R^{11}$, $R^{12}$, and $R^{13}$ in Formula (I) mentioned above, include the above-mentioned arylalkyl groups having 7 to 30 carbon atoms, which are partially or fully substituted with an alkyl group having 1 to 4 carbon atoms, a hydroxyl group, a carboxyl group, a halogen atom, a cyano group, or a nitro group.

Examples of the arylalkyl group having 7 to 30 carbon atoms, substituted with an alkyl group having 1 to 4 carbon atoms, a hydroxyl group, an alkoxy group having 1 to 4 carbon atoms, an amino group, an alkylthio group having 1 to 4 carbon atoms, a carboxyl group, a halogen atom, a cyano group, or a nitro group, and represented by $R^3$, $R^4$, $R^{14}$, $R^{15}$, $R^{16}$, $R^{17}$, and $R^{18}$ in Formula (I) mentioned above, include the above-mentioned arylalkyl groups having 7 to 30 carbon atoms, which are partially or fully substituted with an alkyl group having 1 to 4 carbon atoms, a hydroxyl group, an alkoxy group having 1 to 4 carbon atoms, an amino group, an alkylthio group having 1 to 4 carbon atoms, a carboxyl group, a halogen atom, a cyano group, or a nitro group.

Examples of the alkenyl group having 2 to 12 carbon atoms represented by $R^1$, $R^2$, $R^3$, $R^4$, $R^{14}$, $R^{15}$, $R^{16}$, $R^{17}$, $R^{18}$, and $R^{19}$ in Formula (I) mentioned above include groups such as a vinyl group, a 1-propenyl group, a 2-propenyl group, an isopropenyl group, a 1-butenyl group, a 2-butenyl group, a 3-butenyl group, a 1-octenyl group, and a 1-decenyl group.

Preferable examples of the three- to six-membered heterocycle in Formula (I) mentioned above that may be formed by $R^1$ and $R^2$ binding to each other include a piperidine ring, a piperazine ring, a morpholine ring, and a lactam ring.

Preferable examples of the three- to six-membered cyclic alkane in Formula (I) mentioned above that may be formed by $R^3$ and $R^4$ binding to each other include a cyclopentane ring and a cyclohexane ring.

Examples of the halogen atom with which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ in Formula (I) mentioned above are optionally substituted include fluorine, chlorine, bromine, and iodine.

Examples of the alkyl group having 1 to 4 carbon atoms with which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ in Formula (I) mentioned above are optionally substituted include the alkyl groups having 1 to 4 carbon atoms out of the above-mentioned examples of the unsubstituted alkyl groups having 1 to 12 carbon atoms.

Examples of the heterocyclic group having 2 to 12 carbon atoms represented by $R^{14}$, $R^{15}$, $R^{16}$, $R^{17}$, and $R^{18}$ in Formula (I) mentioned above include five- to seven-membered heterocycles such as a pyridyl, a pyrimidyl, a furyl, a thienyl, a tetrahydrofuryl, a dioxolanyl, a benzoxazol-2-yl, a tetrahydropyranyl, a pyrrolidyl, an imidazolidyl, a pyrazolidyl, a thiazolidyl, an isothiazolidyl, an oxazolidyl, an isooxazolidyl, a piperidyl, a piperazyl, and a morpholinyl.

Examples of the trialkylsilyl group represented by $R^{14}$, $R^{15}$, $R^{16}$, $R^{17}$, and $R^{18}$ in Formula (I) mentioned above include a trimethylsilyl group, a triethylsilyl group, and an ethyldimethylsilyl group, and an example of the triarylsilyl group is a t-butyldiphenylsilyl group.

An alkylene moiety of the group represented by $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ in Formula (I) mentioned above may be interrupted by —O—, —S—, —CO—, —CO—O—, —O—CO—, or —O—CO—O— once to five times in a state in which oxygen atoms are not adjacent to each other. At this time, one or more groups may be used as the interrupting linking group, and interrupting linking groups that can continuously perform interruption may perform the interruption at two or more continuous positions.

In addition, an alkyl (alkylene) moiety of the group represented by $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ in Formula (I) mentioned above may have a branched side chain or may be a cyclic alkyl. Also, the terminus of the alkyl group may have an unsaturated bond such as a double bond or a triple bond.

Of the α-aminoalkylphenone compounds of the present invention, the α-aminoalkylphenone compound in which $R^{11}$ is a nitro group, an alkoxy group having 1 to 12 carbon atoms, or an alkoxycarbonyl group having 1 to 12 carbon atoms is highly sensitive and is easily manufactured, and thus is preferable.

Accordingly, preferable specific examples of the α-aminoalkylphenone compounds according to the present invention represented by Formula (I) mentioned above include the following compounds No. 1 to No. 42. However, the present invention is not limited to the following compounds.

Chemical Formula 2

Compound No. 1

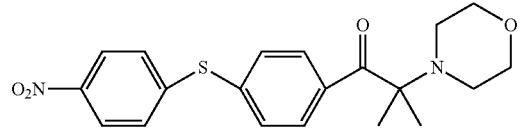

Compound No. 2

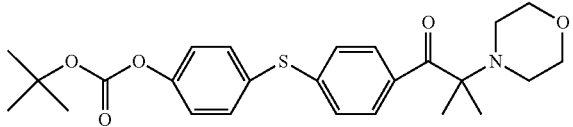

Compound No. 3

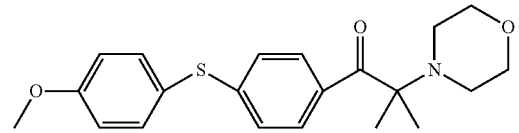

Compound No. 4

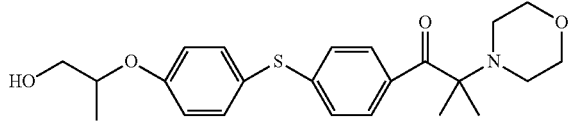

Compound No. 5

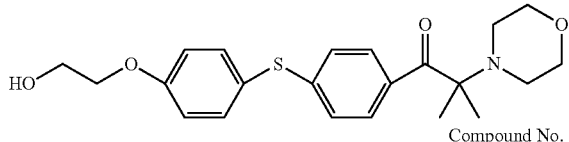

Compound No. 6

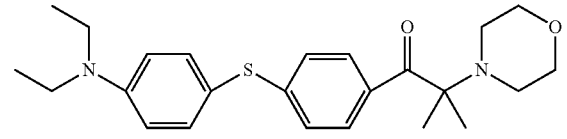

Compound No. 7

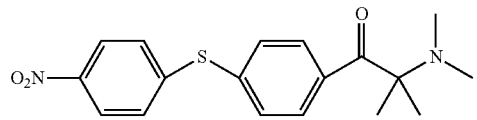

Compound No. 8

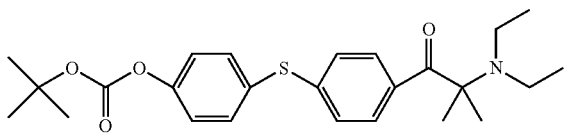

Compound No. 9

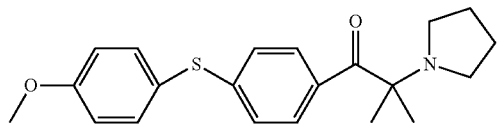

Compound No. 10

Compound No. 11

Compound No. 12

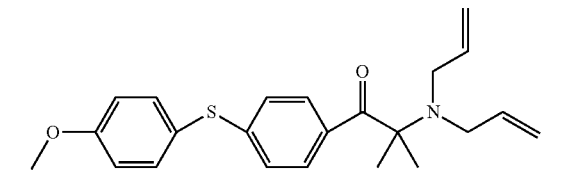

Compound No. 13

Compound No. 14

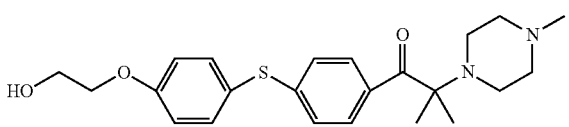

Compound No. 15
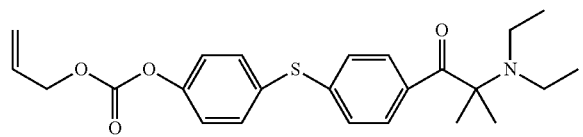
Compound No. 16
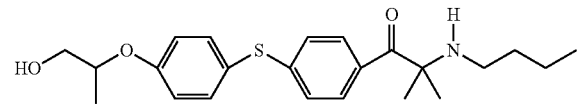
Chemical Formula 3
Compound No. 17
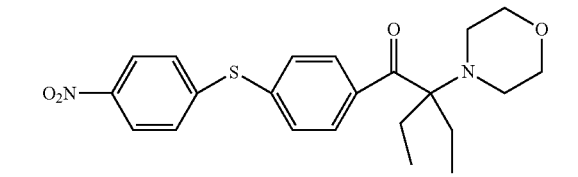
Compound No. 18
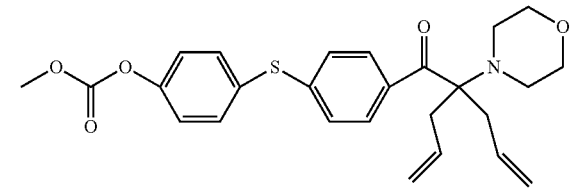
Compound No. 19
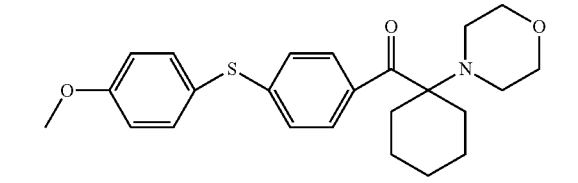
Compound No. 20
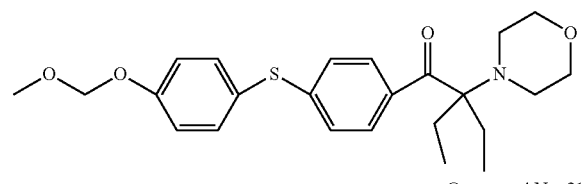
Compound No. 21
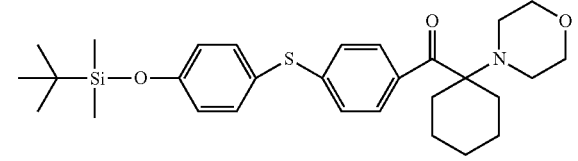
Compound No. 22
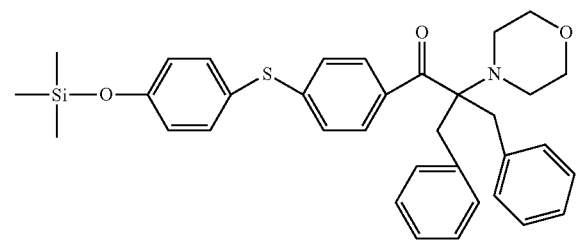
Compound No. 23
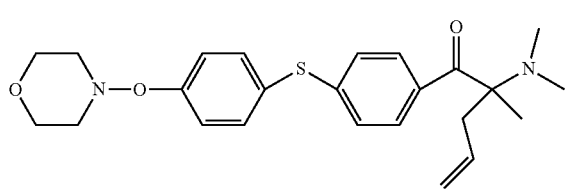
Compound No. 24
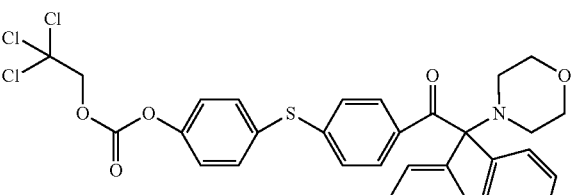
Compound No. 25
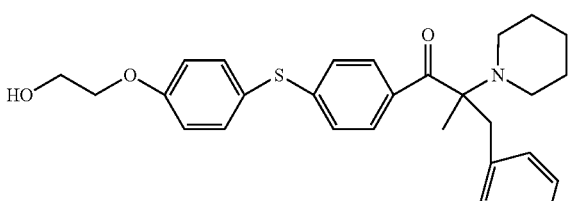
Compound No. 26
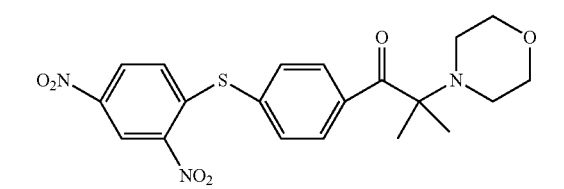
Compound No. 27
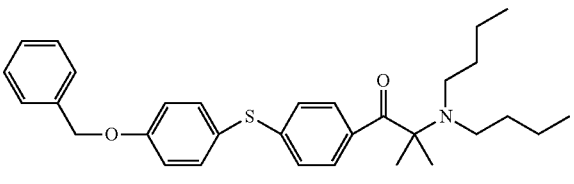
Compound No. 28
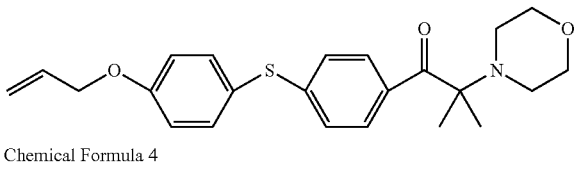
Chemical Formula 4
Compound No. 29
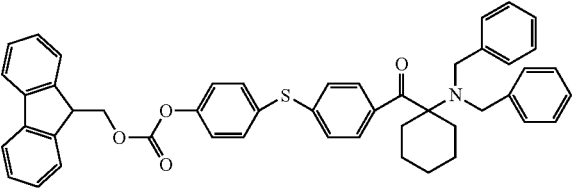

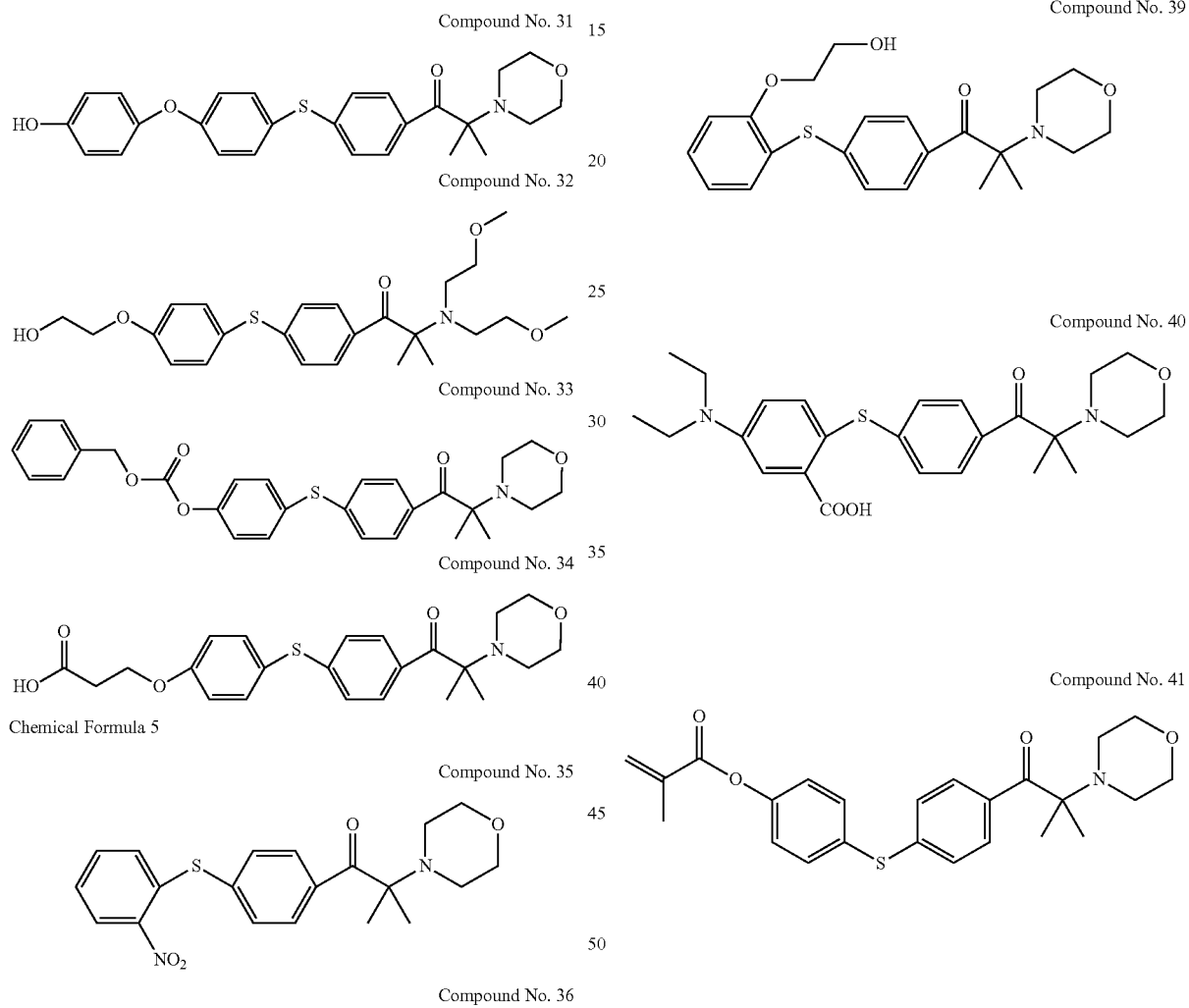
The α-aminoalkylphenone compounds according to the present invention represented by Formula (I) mentioned above can be synthesized by reacting a halogen compound 1 with a thiol compound 1 in accordance with the following scheme, for example.

Chemical Formula 6

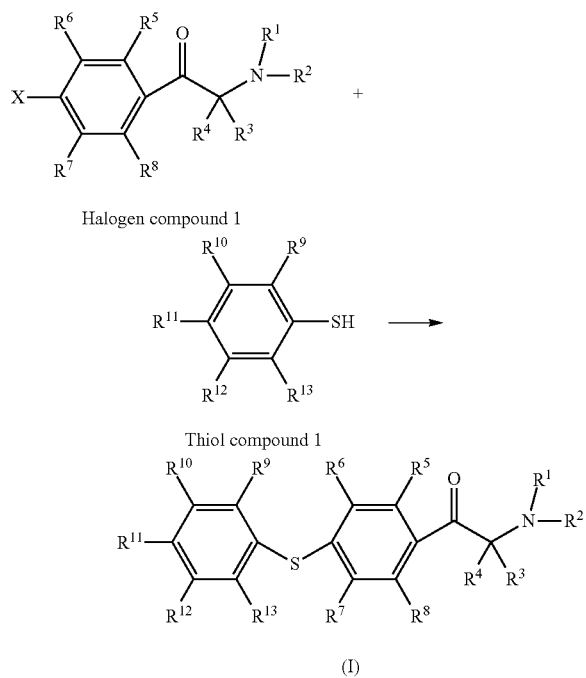

(In the formula, X represents a halogen atom, and $R^1$, $R^2$, $R^3$, $R^4$, $R^5$, $R^6$, $R^7$, $R^8$, $R^9$, $R^{10}$, $R^{11}$, $R^{12}$, and $R^{13}$ are the same as those in Formula (I) mentioned above.)

The novel α-aminoalkylphenone compounds according to the present invention, which have been described above, are useful as a radical polymerization initiator, and particularly a photopolymerization initiator or a thermal polymerization initiator. Also, the novel α-aminoalkylphenone compounds according to the present invention can be preferably used as a sensitizing agent.

The polymerization initiators according to the present invention contain at least one of the α-aminoalkylphenone compounds according to the present invention and are particularly useful as a polymerization initiator for a polymerizable compound having an ethylenically unsaturated bond. The content of the α-aminoalkylphenone compound according to the present invention in the polymerization initiator of the present invention is preferably 30 to 100 mass %, and more preferably 50 to 100 mass %.

The radically polymerizable compositions according to the present invention contain the polymerization initiator of the present invention and a polymerizable compound having an ethylenically unsaturated bond as essential components, and a combination of components such as an alkali-developable compound that may have an ethylenically unsaturated group, an inorganic compound, a coloring material, and a solvent as optional components.

There is no particular limitation on the above-mentioned polymerizable compound having an ethylenically unsaturated bond, and polymerizable compounds that are conventionally used in a radically polymerizable composition can be used. Examples thereof include unsaturated aliphatic hydrocarbons such as ethylene, propylene, butylene, isobutylene, vinyl chloride, vinylidene chloride, vinylidene fluoride, and tetrafluoroethylene; (meth)acrylic acid, α-chloroacrylic acid, itaconic acid, maleic acid, citraconic acid, fumaric acid, himic acid, crotonic acid, isocrotonic acid, vinylacetic acid, allylacetic acid, cinnamic acid, sorbic acid, mesaconic acid, mono[2-(meth)acryloyloxyethyl]succinate, mono[2-(meth)acryloyloxyethyl]phthalate, and mono(meth)acrylates of polymers having a carboxy group and a hydroxyl group at both termini such as ω-carboxypolycaprolactone mono(meth)acrylate; unsaturated polybasic acids such as hydroxyethyl (meth)acrylate malate, hydroxypropyl (meth)acrylate malate, dicyclopentadiene malate, and polyfunctional (meth)acrylates having one carboxyl group and two or more (meth)acryloyl groups; esters between an unsaturated monobasic acid and a polyhydric alcohol or a polyhydric phenol such as 2-hydroxyethyl (meth)acrylate, 2-hydroxypropyl (meth)acrylate, glycidyl acrylate, the compounds No. A1 to No. A4 mentioned below, methyl (meth)acrylate, butyl (meth)acrylate, isobutyl (meth)acrylate, t-butyl (meth)acrylate, cyclohexyl (meth)acrylate, n-octyl (meth)acrylate, isooctyl (meth)acrylate, isononyl (meth)acrylate, stearyl (meth)acrylate, lauryl (meth)acrylate, methoxyethyl (meth)acrylate, dimethylaminomethyl (meth)acrylate, dimethylaminoethyl (meth)acrylate, aminopropyl (meth)acrylate, dimethylaminopropyl (meth)acrylate, ethoxyethyl (meth)acrylate, poly(ethoxy)ethyl (meth)acrylate, butoxyethoxyethyl (meth)acrylate, ethylhexyl (meth)acrylate, phenoxyethyl (meth)acrylate, tetrahydrofuryl (meth)acrylate, vinyl (meth)acrylate, allyl (meth)acrylate, benzyl (meth)acrylate, ethylene glycol di(meth)acrylate, diethylene glycol di(meth)acrylate, triethylene glycol di(meth)acrylate, polyethylene glycol di(meth)acrylate, propylene glycol di(meth)acrylate, 1,4-butanediol di(meth)acrylate, 1,6-hexanediol di(meth)acrylate, trimethylolethane tri(meth)acrylate, trimethylolpropane tri(meth)acrylate, dipentaerythritol hexa(meth)acrylate, dipentaerythritol penta(meth)acrylate, pentaerythritol tetra(meth)acrylate, pentaerythritol tri(meth)acrylate, tricyclodecanedimethylol di(meth)acrylate, tri[(meth)acryloylethyl]isocyanurate, and a polyester (meth)acrylate oligomer; metal salts of unsaturated polybasic acids such as zinc (meth)acrylate and magnesium (meth)acrylate; acid anhydrides of unsaturated polybasic acids such as a maleic anhydride, an itaconic anhydride, a citraconic anhydride, a methyltetrahydrophthalic anhydride, a tetrahydrophthalic anhydride, a trialkyltetrahydrophthalic anhydride, 5-(2,5-dioxotetrahydrofuryl)-3-methyl-3-cyclohexene-1,2-dicarboxylic anhydride, a trialkyltetrahydrophthalic anhydride-maleic anhydride adduct, a dodecenylsuccinic anhydride, and a methylhimic anhydride; amides between an unsaturated monobasic acid and a polyamine such as (meth)acrylamide, methylene bis-(meth)acrylamide, diethylenetriamine tris (meth)acrylamide, xylylene bis(meth)acrylamide, α-chloroacrylamide, and N-2-hydroxyethyl (meth)acrylamide; unsaturated aldehydes such as acrolein; unsaturated nitriles such as (meth)acrylonitrile, α-chloroacrylonitrile, vinylidene cyanide, and allyl cyanide; unsaturated aromatic compounds such as styrene, 4-methylstyrene, 4-ethylstyrene, 4-methoxystyrene, 4-hydroxystyrene, 4-chlorostyrene, divinylbenzene, vinyltoluene, vinylbenzoic acid, vinylphenol, vinylsulfonic acid, 4-vinylbenzenesulfonic acid, vinylbenzyl methyl ether, and vinylbenzyl glycidyl ether; unsaturated ketones such as methyl vinyl ketone; unsaturated amine compounds such as vinylamine, allylamine, N-vinylpyrrolidone, and vinyl piperidine; vinyl alcohols such as allyl alcohol and crotyl alcohol; vinyl ethers such as vinyl methyl ether, vinyl ethyl ether, n-butyl vinyl ether, isobutyl vinyl ether, and allyl glycidyl ether; unsaturated imides such as maleimide, N-phenylmaleimide, and N-cyclohexylmaleimide; indenes such as indene and 1-methylindene; aliphatic conjugated dienes such as 1,3-butadiene, isoprene, and chloroprene; macromonomers having a mono(meth) acryloyl group at the terminus of the molecular chain of the polymer such as polystyrene, polymethyl (meth)acrylate, poly-n-butyl (meth)acrylate, and polysiloxane; vinyl chloride, vinylidene chloride, divinyl succinate, diallyl phthalate, triallyl phosphate, triallyl isocyanurate, vinyl thioether, vinylimidazole, vinyloxazoline, vinylcarbazole, vinylpyrrolidone, vinylpyridine, vinylurethane compounds between a vinyl monomer containing a hydroxyl group and a polyisocyanate compound, and vinyl epoxy compounds between a vinyl monomer containing a hydroxyl group and a polyepoxy compound.

In particular, the polymerization initiator containing the α-aminoalkylphenone compound according to the present invention is preferable for the mono(meth)acrylates of polymers having a carboxy group and a hydroxyl group at both termini, the polyfunctional (meth)acrylates having one carboxy group and two or more (meth)acryloyl groups, and the esters between an unsaturated monobasic acid and a polyhydric alcohol or a polyhydric phenol out of these compounds.

These polymerizable compounds can be used alone or by mixing two or more, and when two or more compounds are mixed and used, these compounds may be copolymerized in advance and used as a copolymer.

Chemical Formula 7

Compound No. A1

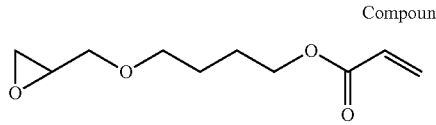

Chemical Formula 8

Compound No. A2

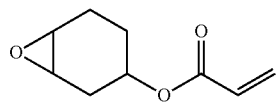

Chemical Formula 9

Compound No. A3

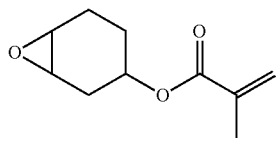

Chemical Formula 10

Compound No. A4

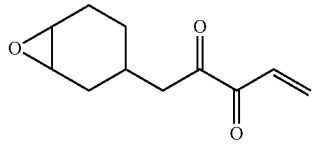

There is no particular limitation on the above-mentioned alkali-developable compounds that may have an ethylenically unsaturated group as long as these compounds are soluble in an alkali aqueous solution, and examples thereof include the resins mentioned in JP 2004-264414A, for example.

As the above-mentioned alkali-developable compounds that may have an ethylenically unsaturated group, a copolymer of an acrylic acid ester, a phenol novolac epoxy resin and/or a cresol novolac epoxy resin, a polyphenylmethane epoxy resin having a polyfunctional epoxy group, an epoxy acrylate resin, and a resin obtained by reacting an unsaturated monobasic acid with the epoxy group of epoxy compounds represented by Formula (III) mentioned below and further reacting a polybasic acid anhydride therewith can be used.

Of these compounds, the resin obtained by reacting an unsaturated monobasic acid with the epoxy group of epoxy compounds represented by Formula (III) mentioned below and further reacting a polybasic acid anhydride therewith is preferable.

In addition, it is preferable that the above-mentioned alkali-developable compounds that may have an ethylenically unsaturated group contain an unsaturated group in an amount of 0.2 to 1.0 equivalents.

Chemical Formula 11

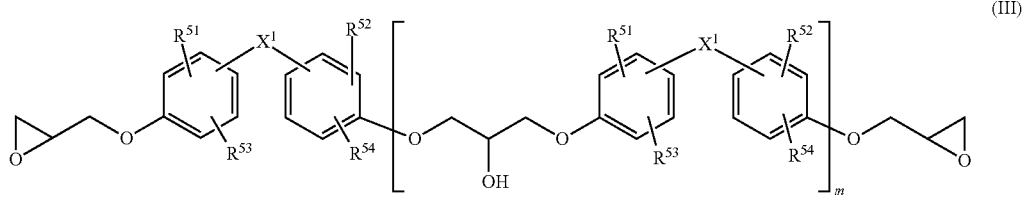

(III)

(In the formula, $X^1$ represents a direct bond, a methylene group, an alkylidene group having 1 to 4 carbon atoms, an alicyclic hydrocarbon group having 3 to 20 carbon atoms, O, S, $SO_2$, SS, SO, CO, OCO, or a group represented by Chemical Formula 12, Chemical Formula 13, or Chemical Formula 14 mentioned below; the above-mentioned alkylidene group is optionally substituted with a halogen atom; $R^{51}$, $R^{52}$, $R^{53}$, and $R^{54}$ each independently represent a hydrogen atom, an alkyl group having 1 to 5 carbon atoms, an alkoxy group having 1 to 8 carbon atoms, an alkenyl group having 2 to 5 carbon atoms, or a halogen atom; the above-mentioned alkyl group, alkoxy group, and alkenyl group are optionally substituted with a halogen atom; m is an integer of 0 to 10; and when m is not 0, any optical isomer may be present.)

Chemical Formula 12

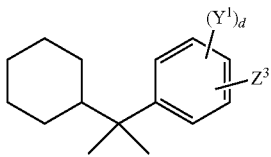

(In the formula, $Z^3$ represents a hydrogen atom, a phenyl group that is optionally substituted with an alkyl group having 1 to 10 carbon atoms or an alkoxy group having 1 to 10 carbon atoms, or a cycloalkyl group having 3 to 10 carbon atoms that is optionally substituted with an alkyl group having 1 to 10 carbon atoms or an alkoxy group having 1 to 10 carbon atoms; $Y^1$ represents an alkyl group having 1 to 10 carbon atoms, an alkoxy group having 1 to 10 carbon atoms, an alkenyl group having 2 to 10 carbon atoms, or a halogen atom; the above-mentioned alkyl group, alkoxy group, and alkenyl group are optionally substituted with a halogen atom; and d is an integer of 0 to 5.)

Chemical Formula 13

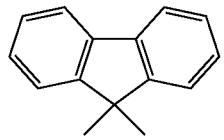

Chemical Formula 14

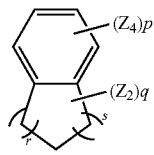

(In the formula, $Y^2$ and $Z^4$ each independently represent an alkyl group having 1 to 10 carbon atoms that is optionally substituted with a halogen atom, an aryl group having 6 to 20 carbon atoms that is optionally substituted with a halogen atom, an aryloxy group having 6 to 20 carbon atoms that is optionally substituted with a halogen atom, an arylthio group having 6 to 20 carbon atoms that is optionally substituted with a halogen atom, an arylalkenyl group having 6 to 20 carbon atoms that is optionally substituted with a halogen atom, an arylalkyl group having 7 to 20 carbon atoms that is optionally substituted with a halogen atom, a heterocyclic group having 2 to 20 carbon atoms that is optionally substituted with a halogen atom, or a halogen atom; an alkylene moiety of the above-mentioned alkyl group and arylalkyl group may be interrupted by an unsaturated bond, —O—, or —S—; $Z^4$s adjacent to each other may form a ring; p represents an integer of 0 to 4; q represents an integer of 0 to 8; r represents an integer of 0 to 4; s represents an integer of 0 to 4; and a total of r and s is an integer of 2 to 4.)

Examples of the above-mentioned unsaturated monobasic acid to be reacted with the above-mentioned epoxy compound include acrylic acid, methacrylic acid, crotonic acid, cinnamic acid, sorbic acid, hydroxyethyl methacrylate malate, hydroxyethyl acrylate malate, hydroxypropyl methacrylate malate, hydroxypropyl acrylate malate, and dicyclopentadiene malate.

Examples of the above-mentioned polybasic acid anhydride, which is reacted after the above-mentioned unsaturated monobasic acid has been reacted, include a biphenyltetracarboxylic dianhydride, a tetrahydrophthalic anhydride, a succinic anhydride, a biphthalic anhydride, a maleic anhydride, a trimellitic anhydride, a pyromellitic anhydride, 2,2'-3,3'-benzophenonetetracarboxylic anhydride, an ethylene glycol bisanhydrotrimellitate, glycerol trisanhydrotrimellitate, hexahydrophthalic anhydride, methyltetrahydrophthalic anhydride, a nadic anhydride, a methylnadic anhydride, a trialkyltetrahydrophthalic anhydride, a hexahydrophthalic anhydride, a 5-(2,5-dioxotetrahydrofuryl)-3-methyl-3-cyclohexene-1,2-dicarboxylic anhydride, a trialkyltetrahydrophthalic anhydride-maleic anhydride adduct, a dodecenylsuccinic anhydride, and a methylhimic anhydride.

It is preferable that the reaction molar ratio of the above-mentioned epoxy compound, monobasic acid, and polybasic acid anhydride is set as follows.

That is, it is preferable that the ratio is set such that in an epoxy adduct that has a structure in which 0.1 to 1.0 carboxyl group of the above-mentioned unsaturated monobasic acid is added with respect to one epoxy group of the above-mentioned epoxy compound, 0.1 to 1.0 acid anhydride structure of the above-mentioned polybasic acid anhydride is present with respect to one hydroxyl group of the epoxy adduct.

The above-mentioned epoxy compound, monobasic acid, and polybasic acid anhydride can be reacted in accordance with a commonly used procedure.

An alkali-developable photosensitive resin composition according to the present invention, which is one embodiment of the radically polymerizable composition according to the present invention, contains the polymerization initiator of the present invention, a polymerizable compound having an ethylenically unsaturated bond, and an alkali-developable compound that may have an ethylenically unsaturated group as essential components, and a combination of components such as an inorganic compound, a coloring material, and a solvent as optional components. It should be noted that, in particular, the alkali-developable photosensitive resin composition according to the present invention containing a coloring material is also referred to as "colored alkali-developable photosensitive resin composition according to the present invention".

The above-mentioned polymerizable compound having an ethylenically unsaturated bond and the above-mentioned alkali-developable compound that may have an ethylenically unsaturated group may be the same compound or different compounds, and may be used alone or in combination of two or more.

In order to improve the developability of the above-mentioned alkali-developable photosensitive resin composition by adjusting the acid value, a monofunctional or polyfunctional epoxy compound can be further used together with the above-mentioned alkali-developable compound that may have an ethylenically unsaturated bond. In the above-mentioned alkali-developable compound that may have an ethylenically unsaturated bond, it is preferable that the acid value of the solid content is in a range from 5 to 120 mgKOH/g, and that the usage amount of the monofunctional or polyfunctional epoxy compound is selected so as to satisfy the above-mentioned acid value.

Examples of the above-mentioned monofunctional epoxy compound include glycidyl methacrylate, methyl glycidyl ether, ethyl glycidyl ether, propyl glycidyl ether, isopropyl glycidyl ether, butyl glycidyl ether, isobutyl glycidyl ether, t-butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, 2-ethylhexyl glycidyl ether, allyl glycidyl ether, propargyl glycidyl ether, p-methoxyethyl glycidyl ether, phenyl glycidyl ether, p-methoxy glycidyl ether, p-butylphenol glycidyl ether, cresyl glycidyl ether, 2-methylcresyl glycidyl ether, 4-nonylphenyl glycidyl ether, benzyl glycidyl ether, p-cumylphenyl glycidyl ether, trityl glycidyl ether, 2,3-epoxypropyl methacrylate, epoxidized soybean oil, epoxidized linseed oil, glycidyl butyrate, vinylcyclohexane monoxide, 1,2-epoxy-4-vinylcyclohexane, styrene oxide, pinene oxide, methylstyrene oxide, cyclohexene oxide, propylene oxide, and compounds No. E1 and No. E2 mentioned below.

Chemical Formula 15

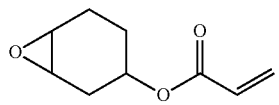

Compound No. E1

Chemical Formula 16

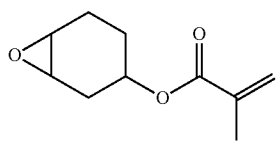

Compound No. E2

It is preferable to use one or more compounds selected from the group consisting of bisphenol epoxy compounds and glycidyl ethers as the above-mentioned polyfunctional epoxy compound because a (colored) alkali-developable photosensitive resin composition having better characteristics can be obtained.

In addition to the epoxy compounds expressed by Formula (III), a bisphenol epoxy compound such as a hydrogenated bisphenol epoxy compound can also be used as the above-mentioned bisphenol epoxy compound, for example.

Ethylene glycol diglycidyl ether, propylene glycol diglycidyl ether, 1,4-butanediol diglycidyl ether, 1,6-hexanediol diglycidyl ether, 1,8-octanediol diglycidyl ether, 1,10-decanediol diglycidyl ether, 2,2-dimethyl-1,3-propanediol diglycidyl ether, diethylene glycol diglycidyl ether, triethylene glycol diglycidyl ether, tetraethylene glycol diglycidyl ether, hexaethylene glycol diglycidyl ether, 1,4-cyclohexanedimethanol diglycidyl ether, 1,1,1-tri(glycidyloxymethyl)propane, 1,1,1-tri(glycidyloxymethyl)ethane, 1,1,1-tri(glycidyloxymethyl)methane, and 1,1,1,1-tetra(glycidyloxymethyl)methane, and the like can be used as the above-mentioned glycidyl ethers.

In addition, novolac epoxy compounds such as a phenol novolac epoxy compound, a biphenyl novolac epoxy compound, a cresol novolac epoxy compound, a bisphenol-A novolac epoxy compound, and a dicyclopentadiene novolac epoxy compound; alicyclic epoxy compounds such as 3,4-epoxy-6-methylcyclohexylmethyl-3,4-epoxy-6-methylcyclohexane carboxylate, 3,4-epoxycyclohexylmethyl-3,4-epoxycyclohexane carboxylate, and 1-epoxyethyl-3,4-epoxycyclohexane; glycidyl esters such as diglycidyl phthalate ester, diglycidyl tetrahydrophthalate ester, and glycidyl dimerate ester; glycidyl amines such as tetraglycidyldiaminodiphenylmethane, triglycidyl P-aminophenol, and N,N-diglycidylaniline; heterocyclic epoxy compounds such as 1,3-diglycidyl-5,5-dimethylhydantoin and triglycidyl isocyanurate; dioxide compounds such as dicyclopentadiene dioxide; naphthalene epoxy compounds; triphenylmethane epoxy compounds; dicyclopentadiene epoxy compounds; and the like can also be used.

Although there is no particular limitation on the content of the polymerization initiator according to the present invention in the radically polymerizable composition according to the present invention, the content of the polymerization initiator is preferably 0.1 to 70 parts by mass, more preferably 1 to 50 parts by mass, and even more preferably 5 to 30 parts by mass, with respect to 100 parts by mass of the above-mentioned polymerizable compound having an ethylenically unsaturated bond.

In particular, when the (colored) alkali-developable photosensitive resin composition is used as the radically polymerizable composition according to the present invention, the content of the above-mentioned alkali-developable compound that may have an ethylenically unsaturated bond in the (colored) alkali-developable photosensitive resin composition according to the present invention is preferably 1 to 20 mass %, and more preferably 3 to 12 mass %.

Furthermore, a solvent can be added to the radically polymerizable composition according to the present invention. A solvent in which the above-mentioned components (the polymerization initiator according to the present invention, the polymerizable compound having an ethylenically unsaturated bond, and the like) can be dissolved or dispersed as needed is generally used as the solvent, and examples thereof include ketones such as methyl ethyl ketone, methyl amyl ketone, diethyl ketone, acetone, methyl isopropyl ketone, methyl isobutyl ketone, cyclohexanone, and 2-heptanone; ether-based solvents such as ethyl ether, dioxane, tetrahydrofuran, 1,2-dimethoxyethane, 1,2-diethoxyethane, and dipropylene glycol dimethyl ether; ester-based solvents such as methyl acetate, ethyl acetate, n-propyl acetate, isopropyl acetate, n-butyl acetate, cyclohexyl acetate, ethyl lactate, dimethyl succinate, and texanol; Cellosolve-based solvents such as ethylene glycol monomethyl ether and ethylene glycol monoethyl ether; alcohol-based solvents such as methanol, ethanol, isopropanol, n-propanol, isobutanol, n-butanol, and amyl alcohol; ether ester-based solvents such as ethylene glycol monomethyl ether acetate, ethylene glycol monoethyl ether acetate, propylene glycol 1-monomethyl ether 2-acetate, dipropylene glycol monomethyl ether acetate, 3-methoxybutyl ether acetate, and ethoxyethyl ether propionate; BTX-based solvents such as benzene, toluene, and xylene; aliphatic hydrocarbon-based solvents such as hexane, heptane, octane, and cyclohexane; terpene-based hydrocarbon oils such as turpentine oil, D-limonene, and pinene; paraffin-based solvents such as mineral spirit, Swasol #310 (Cosmo Matsuyama Oil Co., Ltd.), and Solvesso #100 (ExxonMobil Chemical); halogenated aliphatic hydrocarbon-based solvents such as carbon tetrachloride, chloroform, trichloroethylene, methylene chloride, and 1,2-dichloroethane; halogenated aromatic hydrocarbon-based solvents such as chlorobenzene; Carbitol-based solvents; aniline; triethylamine; pyridine; acetic acid; acetonitrile; carbon disulfide; N,N-dimethylformamide; N,N-dimethylacetamide; N-methylpyrrolidone; dimethylsulfoxide; and water. These solvents can be used as a mixed solvent of one or more.

It is preferable to use the ketones, the ether ester-based solvents, and the like, particularly propylene glycol 1-monomethyl ether 2-acetate, cyclohexanone, and the like, out of these solvents because the radically polymerizable composition has good compatibility between a resist and the polymerization initiator.

A coloring material may be further added to the radically polymerizable composition according to the present invention to produce a colored radically polymerizable composition. Examples of the coloring material include pigments, dyes, and natural coloring matters. These coloring materials can be used alone or by mixing two or more.

An organic pigment or an inorganic pigment can be used as the above-mentioned pigments, and examples thereof include nitroso compounds; nitro compounds; azo compounds; diazo compounds; xanthene compounds; quinoline compounds; anthraquinone compounds; coumarin compounds; phthalocyanine compounds; isoindolinone compounds; isoindolin compounds; quinacridone compounds; anthanthrone compounds; perinone compounds; perylene compounds; diketopyrrolopyrrole compounds; thioindigo compounds; dioxazine compounds; triphenylmethane compounds; quinophthalone compounds; naphthalenetetracarboxylic acids; metal complex compounds such as azo dyes and cyanine dyes; lake pigments; carbon blacks such as those obtained by using a furnace method, a channel method or a thermal method, or acetylene black, Ketjen black, or lamp black; the above-mentioned carbon blacks that have been adjusted or coated with an epoxy resin, the above-mentioned carbon blacks that have undergone a dispersion treatment using a resin in a solvent in advance and absorbed the resin to an amount of 20 to 200 mg/g, the above-mentioned carbon blacks that have undergone an acidic or alkaline surface treatment, the above-mentioned carbon blacks having an average particle diameter of 8 nm or more and a DBP oil absorption amount of 90 ml/100 g or less, and the carbon blacks having a total oxygen amount calculated from CO and $CO_2$ in volatile components at 950° C. of 9 mg or more with respect to 100 $m^2$ of the surface area of the carbon black; graphite, graphitized carbon black, active carbon, carbon fibers, carbon nanotubes, carbon microcoils, carbon nanohorns, carbon aerogels, and fullerene; aniline black, Pigment Black 7, and titanium black; chromic oxide green, Milori blue, cobalt green, cobalt blue, manganese-based pigments, ferrocyanides, phosphate ultramarine blue, Prussian blue, ultramarine, cerulean blue, viridian, emerald green, lead sulfate, yellow lead, zinc yellow, Bengal red (red iron oxide (III)), cadmium red, synthetic iron black, and amber. These pigments can be used alone or by mixing a plurality thereof.

Commercially available pigments can also be used as the above-mentioned pigments, and examples thereof include Pigment Red 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, and 254; Pigment Orange 13, 31, 34, 36, 38, 43, 46, 48, 49, 51, 52, 55, 59, 60, 61, 62, 64, 65, and 71; Pigment Yellow 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; Pigment Green 7, 10, and 36; Pigment Blue 15, 15:1, 15:2, 15:3, 15:4, 15:5, 15:6, 22, 24, 56, 60, 61, 62, and 64; and Pigment Violet 1, 19, 23, 27, 29, 30, 32, 37, 40, and 50.

Examples of the above-mentioned dyes include dyes such as azo dyes, anthraquinone dyes, indigoid dyes, triarylmethane dyes, xanthene dyes, alizarin dyes, acridine dyes, stilbene dyes, thiazole dyes, naphthol dyes, quinoline dyes, nitro dyes, indamine dyes, oxazine dyes, phthalocyanine dyes, and cyanine dyes. These dyes may be used by mixing a plurality thereof.

The content of the above-mentioned coloring material in the radically polymerizable composition according to the present invention is preferably 50 to 350 parts by mass, and more preferably 100 to 250 parts by mass, with respect to 100 parts by mass of the above-mentioned polymerizable compound having an ethylenically unsaturated bond.

Furthermore, an inorganic compound can be added to the radically polymerizable composition according to the present invention. Examples of the inorganic compound include metal oxides such as nickel oxide, iron oxide, iridium oxide, titanium oxide, zinc oxide, magnesium oxide, calcium oxide, potassium oxide, silica, and alumina; layered clay minerals, Milori blue, calcium carbonate, magnesium carbonate, cobalt-based compounds, manganese-based compounds, glass powder (particularly glass frit), mica, talc, kaolin, ferrocyanides, various metal sulfates, sulfides, selenides, aluminum silicate, calcium silicate, aluminum hydroxide, platinum, gold, silver, and copper.

Of these, glass frit, titanium oxide, silica, layered clay minerals, silver, and the like are preferable. The content of the above-mentioned inorganic compound in the radically polymerizable composition according to the present invention is preferably 0.1 to 1000 parts by mass, and more preferably 10 to 800 parts by mass, with respect to 100 parts by mass of the above-mentioned polymerizable compound having an ethylenically unsaturated bond. It should be noted that one or more of these inorganic compounds can be used.

These inorganic compounds are used as a filler, an antireflection agent, a conducting agent, a stabilizer, a flame retardant, a mechanical strength improving agent, a special-wavelength absorber, an ink repellent, and the like, for example.

A dispersant used to disperse the coloring material and/or the inorganic compound can be added to the radically polymerizable composition according to the present invention. There is no limitation on the dispersant as long as the dispersant can be used to disperse and stabilize the coloring material or the inorganic compound, and commercially available dispersants such as BYK series manufactured by BYK Chemie can be used as the dispersant. In particular, polymeric dispersants including polyester, polyether, or polyurethane having a basic functional group are preferably used, the basic functional group having a nitrogen atom, the functional group having a nitrogen atom being amine and/or quaternary salts thereof, and the amine value being 1 to 100 mgKOH/g.

In the radically polymerizable composition according to the present invention, other polymerization initiators can be used together with the α-aminoalkylphenone compound according to the present invention. Examples of the other polymerization initiators include photopolymerization initiators and thermal polymerization initiators.

Conventionally known compounds can be used as the other photopolymerization initiators, and examples thereof include benzophenone, phenyl biphenyl ketone, 1-hydroxy-1-benzoylcyclohexane, benzoin, benzyl dimethyl ketal, 1-benzyl-1-dimethylamino-1-(4'-morpholinobenzoyl)propane, 2-morpholyl-2-(4'-methylmercapto)benzoylpropane, thioxanthone, 1-chloro-4-propoxythioxanthone, isopropylthioxanthone, diethylthioxanthone, ethylanthraquinone, 4-benzoyl-4'-methyldiphenylsulfide, benzoin butyl ether, 2-hydroxy-2-benzoylpropane, 2-hydroxy-2-(4'-isopropyl)benzoylpropane, 4-butylbenzoyltrichloromethane, 4-phenoxybenzoyldichloromethane, methyl benzoylformate, 1,7-bis(9'-acridinyl)heptane, 9-n-butyl-3,6-bis(2'-morpholinoisobutyroyl)carbazole, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, 2,2-bis(2-chlorophenyl)-4,5,4',5'-tetraphenyl-1-2'-biimidazole, 4,4-azobisisobutyronitrile, triphenylphosphine, camphorquinone, N-1414, N-1717, N-1919, NCI-831, NCI-930 (manufactured by ADEKA Corporation), IRGACURE369, IRGACURE907, IRGACURE OXE 01, IRGACURE OXE 02 (manufactured by BASF), TR-PBG-304, TR-PBG-305, TR-PBG-314 (manufactured by Tronly), benzoyl peroxide, and compounds represented by Formula (IV) mentioned below. It is preferable that the usage amount of the other photopolymerization initiator in terms of mass is less than or equal to the usage amount of the α-aminoalkylphenone compound according to the present invention. It should be noted that these photopolymerization initiators can be used alone or in combination of two or more.

Chemical Formula 17

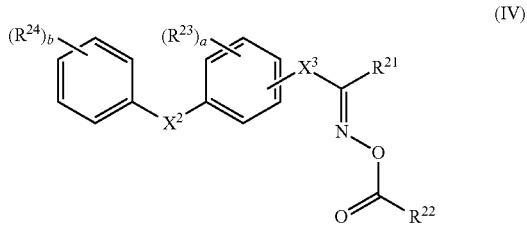

(IV)

(In the formula, $R^{21}$ and $R^{22}$ each independently represent a hydrogen atom, a cyano group, an alkyl group having 1 to 20 carbon atoms, an aryl group having 6 to 30 carbon atoms, an arylalkyl group having 7 to 30 carbon atoms, or a heterocyclic group having 2 to 20 carbon atoms, $R^{23}$ and $R^{24}$ each independently represent a halogen atom, a nitro group, a cyano group, a hydroxyl group, a carboxyl group, $R^{25}$, $OR^{26}$, $SR^{27}$, $NR^{28}R^{29}$, $COR^{30}$, $SOR^{31}$, $SO_2R^{32}$, or $CONR^{33}R^{34}$, and $R^{23}$ and $R^{24}$ may bind to each other to form a ring, $R^{25}$, $R^{26}$, $R^{27}$, $R^{28}$, $R^{29}$, $R^{30}$, $R^{31}$, $R^{32}$, $R^{33}$, and $R^{34}$ each independently represent an alkyl group having 1 to 20 carbon atoms, an aryl group having 6 to 30 carbon atoms, an arylalkyl group having 7 to 30 carbon atoms, or a heterocyclic group having 2 to 20 carbon atoms, $X^2$ represents an oxygen atom, a sulfur atom, a selenium atom, $CR^{35}R^{36}$, CO, $NR^{37}$, or $PR^{38}$, $X^3$ represents a single bond or CO, $R^{35}$, $R^{36}$, $R^{37}$, and $R^{38}$ represent an alkyl group having 1 to 20 carbon atoms, an aryl group having 6 to 30 carbon atoms or an arylalkyl group having 7 to 30 carbon atoms, a methylene group in the alkyl group or the arylalkyl group is optionally substituted with a halogen atom, a nitro group, a cyano group, a hydroxyl group, a carboxyl group, or a heterocyclic group and interrupted by —O—, $R^{35}$, $R^{36}$, $R^{37}$, and $R^{38}$ independently may form a ring together with one of the adjacent benzene rings, a represents an integer of 0 to 4, and b represents an integer of 0 to 5.)

Examples of the other thermal polymerization initiators include azo initiators such as 2,2'-azobisisobutyronitrile, 2,2'-azobis(methylisobutyrate), 2,2'-azobis-2,4-dimethylvaleronitrile, and 1,1'-azobis(1-acetoxy-1-phenylethane); peroxide initiators such as benzoyl peroxide, di-t-butylbenzoyl peroxide, t-butyl peroxypivalate, and di(4-t-butylcyclohexyl) peroxydicarbonate; and persulfates such as ammonium persulfate, sodium persulfate, and potassium persulfate. These initiators can be used by mixing one or more.

Commonly used additives such as a photo/thermal acid generator; a thermal polymerization suppressing agent such as p-anisole, hydroquinone, pyrocatechol, t-butylcatechol, or phenothiazine; a plasticizer; an adhesion accelerator; a filler; an antifoaming agent; a leveling agent, a surface adjusting agent; an antioxidant; an ultraviolet absorber; a dispersion assistant; an aggregation preventing agent; a catalyst; a curing accelerator; a cross-linking agent; and a thickening agent can be added to the radically polymerizable composition according to the present invention as needed.

Although the usage amounts of the optional components (except the above-mentioned other photopolymerization initiator, alkali-developable compound that may have an ethylenically unsaturated group, inorganic compound (filler), coloring material, and solvent) other than the above-mentioned polymerizable compound having an ethylenically unsaturated bond and the α-aminoalkylphenone compound according to the present invention are selected as appropriate based on the purposes for which the optional components are used, and are not particularly limited, the total usage amount thereof is preferably not more than 50 parts by mass with respect to 100 parts by mass of the above-mentioned polymerizable compound having an ethylenically unsaturated bond.

Moreover, the characteristics of a cured product can also be improved by using other organic polymers together with the polymerizable compound having an ethylenically unsaturated bond in the radically polymerizable composition according to the present invention. Examples of the organic polymers include polystyrene, polymethyl methacrylate, a methyl methacrylate-ethyl acrylate copolymer, poly(meth)acrylic acid, a styrene-(meth)acrylic acid copolymer, a (meth)acrylic acid-methyl methacrylate copolymer, an ethylene-vinyl chloride copolymer, an ethylene-vinyl copolymer, a polyvinyl chloride resin, an ABS resin, nylon 6, nylon 66, nylon 12, a urethane resin, polycarbonate polyvinyl butyral, cellulose ester, polyacrylamide, saturated polyester, a phenol resin, a phenoxy resin, a polyamideimide resin, a polyamic acid resin, and an epoxy resin. Of these, polystyrene, a (meth)acrylic acid-methyl methacrylate copolymer, and an epoxy resin are preferable.

When the other organic polymers are used, the usage amount thereof is preferably 10 to 500 parts by mass with respect to 100 parts by mass of the above-mentioned polymerizable compound having an ethylenically unsaturated bond.

Furthermore, a chain transfer agent, a sensitizer, a surfactant, a silane coupling agent, melamine, and the like can also be used together in the radically polymerizable composition according to the present invention.

A compound containing a sulfur atom is usually used as the above-mentioned chain transfer agent or sensitizer. Examples thereof include mercapto compounds such as thioglycolic acid, thiomalic acid, thiosalicylic acid, 2-mercaptopropionic acid, 3-mercaptopropionic acid, 3-mercaptobutyric acid, N-(2-mercaptopropionyl)glycine, 2-mercaptonicotinic acid, 3-[N-(2-mercaptoethyl)carbamoyl]propionic acid, 3-[N-(2-mercaptoethyl)amino]propionic acid, N-(3-mercaptopropionyl)alanine, 2-mercaptoethanesulfonic acid, 3-mercaptopropanesulfonic acid, 4-mercaptobutanesulfonic acid, dodecyl(4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercaptobenzoimidazole, 2-mercapto-3-pyridinol, 2-mercaptobenzothiazole, mercaptoacetic acid, trimethylolpropane tris(3-mercaptopropionate), and pentaerythritol tetrakis(3-mercaptopropionate); disulfide compounds obtained by oxidizing the mercapto compounds; alkyl iodide compounds such as iodoacetic acid, iodopropionic acid, 2-iodoethanol, 2-iodoethanesulfonic acid, and 3-iodopropanesulfonic acid; polyfunctional aliphatic thiol compounds such as trimethylolpropane tris(3-mercaptoisobutyrate), butanediol bis(3-mercaptoisobutyrate), hexanedithiol, decanedithiol, 1,4-dimethylmercaptobenzene, butanediol bisthiopropionate, butanediol bisthioglycolate, ethylene glycol bisthioglycolate, trimethylolpropane tristhioglycolate, butanediol bisthiopropionate, trimethilolpropane tristhiopropionate, trimethylolpropane tristhioglycolate, pentaerythritol tetrakisthiopropionate, pentaerythritol tetrakisthioglycolate, trishydroxyethyl tristhiopropionate, diethylthioxanthone, diisopropylthioxanthone, a compound No. C1 mentioned below, trimercaptopropionate tris(2-hydroxyethyl)isocyanurate; and Karenz MT BD1, PE1, and NR1 manufactured by Showa Denko K.K.

Chemical Formula 18

Compound No. C1

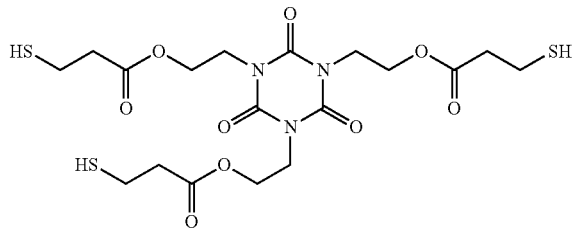

Surfactants including fluorine-containing surfactants such as perfluoroalkylphosphoric acid esters and perfluoroalkylcarboxylates; anionic surfactants such as alkali salts of higher fatty acids, alkylsulfonates, and alkylsulfates; cationic surfactants such as halogen acid salts of higher amines and quaternary ammonium salts; nonionic surfactants such as polyethylene glycol alkyl ether, polyethylene glycol fatty acid ester, sorbitan fatty acid ester, and fatty acid monoglycerides; amphoteric surfactants; and silicone-based surfactants can be used as the above-mentioned surfactant. These surfactants may be used in combination.

Silane coupling agents manufactured by Shin-Etsu Chemical Co., Ltd. can be used as the above-mentioned silane coupling agent, for example. In particular, silane coupling agents having an isocyanate group, a methacryloyl group, or an epoxy group, such as KBE-9007, KBM-502, and KBE-403, are preferably used.

Examples of the above-mentioned melamine compound include compounds in which all of or a part (at least two) of the active methylol groups ($CH_2OH$ groups) in nitrogen-containing compounds such as (poly)methylolmelamine, (poly)methylolglycoluril, (poly)methylolbenzoguanamine, and (poly)methylolurea are alkyl-etherified.

Here, examples of the alkyl groups included in the alkyl ether include a methyl group, an ethyl group and a butyl group, and the alkyl groups may be the same or different. Moreover, methylol groups that have not been alkyl-etherified may be self-condensed in one molecule or may be condensed between two molecules to form an oligomer component.

Specifically, hexamethoxymethylmelamine, hexabutoxymethylmelamine, tetramethoxymethylglycoluril, and tetrabutoxymethylglycoluril, and the like can be used.

Of these, alkyl-etherified melamines such as hexamethoxymethylmelamine and hexabutoxymethylmelamine are preferable.

The radically polymerizable composition according to the present invention can be applied to a support base made of soda glass, quartz glass, a semiconductor substrate, metal, paper, plastics, or the like by a known means such as a spin coater, a roll coater, a bar coater, a die coater, a curtain coater, various types of printing, and immersion. Also, the radically polymerizable composition can be once applied to a support base such as a film and then transferred to another support base, and there is no limitation on the application method.

A high-energy beam having a wavelength of 2,000 angstroms to 7,000 angstroms such as electromagnetic wave energy, an electron beam, an X-ray, or radiation that are emitted by an ultra high-pressure mercury lamp, a high-pressure mercury lamp, a medium-pressure mercury lamp, a low-pressure mercury lamp, a mercury vapor arc lamp, a xenon arc lamp, a carbon arc lamp, a metal halide lamp, a fluorescent lamp, a tungsten lamp, an excimer lamp, a sterilization lamp, a light-emitting diode, and a CRT light source, or the like can be used as a light source of an energy beam to be used to cure the radically polymerizable composition according to the present invention. It is preferable to use the ultra high-pressure mercury lamp, the mercury vapor arc lamp, the carbon arc lamp, the xenon arc lamp, and the like that emit light having a wavelength of 300 to 450 nm.

Furthermore, a laser direct imaging method in which an image is formed directly from digital information provided by a computer or the like using a laser beam as an exposure light source without a mask is useful because not only productivity but also resolution, position accuracy, and the like can be enhanced. Light having a wavelength of 340 to 430 nm is preferably used as the laser beam, and light sources that emit light from a visible region to an infrared region such as an excimer laser, a nitrogen laser, an argon ion laser, a helium cadmium laser, a helium neon laser, a krypton ion laser, various semiconductor lasers, and a YAG laser are also used. When these lasers are used, a sensitizing dye that absorbs light from a visible region to an infrared region will be added.

The radically polymerizable composition according to the present invention can be used in various applications including a photo-curing paint or varnish; a photo-curing adhesive; a printed substrate; a color filter in a liquid crystal color display element of a color television, a PC monitor, a mobile information terminal, a digital camera, and the like; a color filter in a CCD image sensor; a material of an electrode for a plasma display panel; a powder coating; a printing plate; an adhesive; a dental composition; a gel coat; a photoresist for electronics; an electroplating resist; an etching resist; a solder resist; a resist to be used in manufacturing of a color filter for various display applications or formation of a structure in a process for manufacturing a plasma display panel, an electric light-emitting display device, and an LCD; a composition in which an electric or electronic part is sealed; a magnetic recording material; a minute machine part; a waveguide; an optical switch; a plating mask; an etching mask; a color testing system; glass fiber cable coating; a stencil for screen printing; a material for manufacturing a three-dimensional object by using stereo lithography; a holography recording material; an image recording material; a minute electronic circuit; a decoloring material; a decoloring material for an image recording material; a decoloring material for an image recording material using a microcapsule; a photoresist material for a printed wiring board; a photoresist material for a direct imaging system using a UV laser or a visible laser; a photoresist material or protective film to be used in formation of a dielectric layer when layers are laminated on a printed circuit board, and there is no particular limitation on the applications.

The radically polymerizable composition according to the present invention can also be used to form a spacer for a liquid crystal display panel and a projection for a vertical alignment type liquid crystal display element. In particular, the radically polymerizable composition according to the present invention is useful as a photosensitive composition for simultaneously forming a projection and a spacer for a vertical alignment type liquid crystal display element.

The above-mentioned spacer for a liquid crystal display panel is preferably formed by (1) a step of forming a coating of the radically polymerizable composition according to the present invention on a substrate, (2) a step of irradiating the coating with radiation via a mask having a predetermined pattern shape, (3) a baking step after exposure, (4) a step of developing the exposed coating, and (5) a step of heating the developed coating.

The radically polymerizable composition to which an ink repellent has been added is useful as a resin composition for forming a partition for an inkjet system. The composition is used for a color filter, and particularly preferably for a partition for an inkjet color filter having a profile angle of 50° or more. A fluorine-based surfactant and a composition including the fluorine-based surfactant are preferably used as the ink repellent.

An optical element is manufactured by using a method in which partitions made of the radically polymerizable composition according to the present invention divide the surface of a transfer object, and image regions are formed by applying droplets to recessed portions on the divided transfer object by using an inkjet method. At this time, it is preferable that the droplets contain coloring agents and the image regions are colored, and an optical element that has at least a pixel group including a plurality of colored regions and partitions for separating the colored regions in the pixel group on a substrate, and that is produced with the above-mentioned method for manufacturing an optical element is preferably used.

The radically polymerizable composition according to the present invention is also used as a composition for a protective film or an insulating film, and may contain an ultraviolet absorber, an alkylation-modified melamine and/or acryl-modified melamine, a monofunctional or bifunctional (meth)acrylate monomer containing an alcoholic hydroxyl group in the molecule, and/or silica sol.

As the above-mentioned radically polymerizable composition for a protective film or an insulating film, it is preferable to use a resin composition containing the following as main components:

(A) a resin containing a carboxyl group that is obtained by reacting a diol compound with a polycarboxylic acid and has a weight-average molecular weight of 2,000 to 40,000 and an acid value of 50 to 200 mgKOH/g;

(B) an unsaturated compound that contains at least one photopolymerizable ethylenically unsaturated bond in one molecule;

(C) an epoxy compound; and (D) a polymerization initiator that contains an α-aminoalkylphenone compound represented by Formula (I) mentioned above, the resin composition containing 10 to 40 parts by weight of component (C) and 0.1 to 20 parts by weight of component (D) with respect to 100 parts by weight of component (A) and component (B) in total.

In a laminated body in which an insulating resin layer is provided on a support base that can be taken off, the above-mentioned insulating film is used for the insulating layer, and it is preferable that the laminated body can be developed using an alkali aqueous solution and the insulating resin layer has a thickness of 3 to 100 μm.

The radically polymerizable composition according to the present invention to which an inorganic material (inorganic compound) has been added can be used as a photosensitive paste composition. The photosensitive paste composition is used to form a calcined pattern such as a partition pattern, a dielectric pattern, an electrode pattern, and a black matrix pattern of a plasma display panel.

EXAMPLES

Hereinafter, the present invention will be described more specifically by way of examples and comparative examples, but the present invention is not limited to the examples and the like.

Example 1-1

Manufacturing of Compound No. 5

1.0 eq. of a halogen compound 1 was dissolved in 11.0 eq. of dimethylsulfoxide, and 3.0 eq. of potassium carbonate and 1.3 eq. of a thiol compound 1 were added to the resultant solution. Then, the resultant mixture was heated and stirred in a nitrogen atmosphere at 70° C. for 16 hours. The mixture was cooled to room temperature, and then extracted using ethyl acetate. The solvent was distilled off, and the crude product was recrystallized from a solution of methanol:ion-exchanged water=1:1 and dried. Thus, an intermediate 1 (yield: 22.9%) represented by Chemical Formula 19 mentioned below was obtained.

1.0 eq. of the intermediate 1 was dissolved in 14.0 eq. of o-xylene, and 1.1 eq. of ethylene carbonate and 0.02 eq. of potassium carbonate were added to the resultant solution. Then, the resultant mixture was stirred in a nitrogen atmosphere at 140° C. for 18 hours. The mixture was cooled to room temperature, and then extracted using ethyl acetate. The solvent was distilled off, and the crude product was purified by silica column chromatography (n-hexane:ethyl acetate=1:1) and dried. Thus, a compound No. 5 (yield: 69.0%) was obtained.

It should be noted that the halogen compound 1 in Chemical Formula 6 in which $R^1$ and $R^2$ form a morpholine ring, $R^3$ and $R^4$ are methyl groups, $R^5$, $R^6$, $R^7$, and $R^8$ are hydrogen atoms, and X is a bromine atom was used as the halogen compound 1 in this manufacturing example. In addition, the thiol compound 1 in Chemical Formula 6 in which $R^9$, $R^{10}$, $R^{12}$, and $R^{13}$ are hydrogen atoms, and $R^{11}$ is a hydroxyl group was used as the thiol compound 1.

Table 1 to Table 3 show the analysis results.

Chemical Formula 19

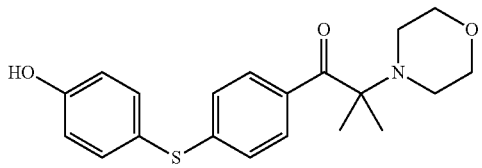

Example 1-2

Manufacturing of Compound No. 8

1.0 eq. of the intermediate 1 obtained in Example 1-1 was placed in a 100-ml four-neck flask. 7.0 eq. of ethyl acetate was added thereto, and the intermediate 1 was dissolved. 0.4 eq. of dimethylaminopyridine and 1.5 eq. of di-t-butyl dicarbonate were added, and the resultant mixture was stirred in a nitrogen atmosphere at room temperature for 4 hours. The reaction liquid was washed three times using ion-exchanged water, and then the solvent was distilled off. The crude product was dissolved in n-hexane, and the solvent was completely removed by vacuum drying. Thus, a compound No. 8 (yield: 41.6%) was obtained.

Table 1 to Table 3 show the analysis results.

Example 1-3

Manufacturing of Compound No. 41

1.0 eq. of the intermediate 1 obtained in Example 1-1 was placed in a 50-ml four-neck flask and dissolved in 32.4 eq. of tetrahydropyran. 0.005 eq. of 2,6-di-t-butyl-4-hydroxytoluene was added thereto, and the resultant mixture was stirred under ice-cooling. 1.7 eq. of triethylamine was added dropwise, and then 1.7 eq. of methacrylic acid chloride was added dropwise. The resultant mixture was stirred under ice-cooling for 4 hours, and then extracted using ethyl acetate. The solvent was distilled off, and the crude product was purified by silica column chromatography (n-hexane:ethyl acetate=5:1) and dried. Thus, a compound No. 41 (yield: 43.1%) was obtained.

Table 1 to Table 3 show the analysis results.

Example 1-4

Manufacturing of Compound No. 42

1.0 eq. of the intermediate 1 obtained in Example 1-1 was placed in a 50-ml four-neck flask and dissolved in 14.3 eq. of dimethylacetamide. 1.1 eq. of propylene carbonate and 0.02 eq. of potassium carbonate were added thereto, and the resultant mixture was stirred at 150° C. for 10 hours. The mixture was cooled to room temperature, extracted using ethyl acetate, and washed twice using ion-exchanged water. The solvent was distilled off, and the crude product was purified by silica column chromatography (n-hexane:ethyl acetate=1:1) and dried. Thus, a compound No. 42 (yield: 42.4%) was obtained.

Table 1 to Table 3 show the analysis results.

TABLE 1

| | Compound | Melting point (° C.) | Decomposition point (° C.) |
|---|---|---|---|
| Example 1-1 | Compound No. 5 | 110 | 283 |
| Example 1-2 | Compound No. 8 | 126 | 149 |
| Example 1-3 | Compound No. 41 | — | 273 |
| Example 1-4 | Compound No. 42 | 97 | 294 |

TABLE 2

| | Chemical shift/ppm (multiplicity, proton number) |
|---|---|
| Compound No. 5 (CDCl$_3$) | 8.42 (d, 2H), 7.48 (d, 2H), 7.04 (d, 2H), 6.98 (d, 2H), 4.12 (t, 2H), 4.00 (t, 2H), 3.66 (t, 4H), 2.54 (t, 4H), 2.07 (s, 1H), 1.28 (s, 6H) |
| Compound No. 8 (CDCl$_3$) | 8.45 (d, 2H), 7.52 (d, 2H), 7.23 (d, 2H), 7.15 (d, 2H), 3.67 (t, 4H), 2.55 (t, 4H), 1.57 (s, 9H), 1.29 (s, 6H) |
| Compound No. 41 (CDCl$_3$) | 8.45 (d, 2H), 7.54 (d, 2H), 7.19 (d, 2H), 7.16 (d, 2H), 6.37 (s, 1H), 5.79 (s, 1H), 3.66 (t, 4H), 2.56 (t, 4H), 2.08 (s, 3H), 1.29 (s, 6H) |
| Compound No. 42 (CDCl$_3$) | 8.42 (d, 2H), 7.48 (d, 2H), 7.03 (d, 2H), 6.97 (d, 2H), 4.23 (s, 1H), 3.98 (dd, 1H), 3.85 (t, 1H), 3.66 (t, 4H), 2.54 (t, 4H), 2.31 (s, 1H), 1.31 (d, 3H), 1.29 (s, 6H) |

TABLE 3

| | IR absorption spectrum/cm$^{-1}$ |
|---|---|
| Compound No. 5 | 3494, 2971, 2931, 2868, 2826, 1739, 1674, 1584, 1493, 1449, 1365, 1251, 1109, 1080, 881, 826 |
| Compound No. 8 | 2942, 1751, 1670, 1581, 1367, 1274, 1257, 1139, 1078, 1012, 881 |
| Compound No. 41 | 2957, 2851, 1736, 1672, 1584, 1488, 1291, 1258, 1201, 1117, 879 |
| Compound No. 42 | 3469, 2972, 2842, 1669, 1586, 1493, 1450, 1287, 1237, 1110, 883, 845 |

Example 2-1 to Example 2-4

Manufacturing of Radically Polymerizable Compositions No. 1 to No. 4

54.84 g of SPC-1000 (acrylic resin; manufactured by Showa Denko K.K.), 12.77 g of Aronix M-450 (polyfunctional acrylate; manufactured by Toagosei Co., Ltd.), 0.57 g of KBE-403 (silane coupling agent; manufactured by Shin-Etsu Sillicone), 3.19 g of a 1% solution of FZ-2122 (surfactant; manufactured by Nippon Unicar Co., Ltd.) in cyclohexanone, and 27.95 g of propylene glycol 1-monomethyl ether 2-acetate were mixed, and 14.805 g of the mixed liquid was weighed. 0.195 g of the compound No. 5, No. 8, No. 41 or No. 42 obtained in Examples 1-1 to 1-4 was added thereto, and the resultant mixture was stirred well. Thus, radically polymerizable compositions No. 1 to No. 4, which are the radically polymerizable compositions according to the present invention, were obtained.

Comparative Example 2-1

Manufacturing of Comparative Radically Polymerizable Composition No. 1

A comparative radically polymerizable composition No. 1 was obtained with the same method as that in Example 2-1, except that 2-morpholyl-2-(4'-methylmercapto)benzoylpropane was used instead of the compound No. 5 obtained in Example 1-1.

Evaluation Examples 1-1 to 1-3 and Comparative Evaluation Example 1-1

Evaluation of Sublimability

The sublimability of the compounds No. 5, No. 41 and No. 42, and the comparative compound (2-morpholyl-2-(4'-methylmercapto)benzoylpropane) was evaluated as follows.

That is, 2.5 mg of the compound was kept in a nitrogen atmosphere at 150° C. for 1 hour, the ratio of a decrease in weight was calculated, and thus the sublimability was evaluated. Table 4 shows the test results.

TABLE 4

| Compound | ΔDecrease in weight (%) |
|---|---|
| No. 5 | 0.3 |
| No. 41 | 0.6 |
| No. 42 | 1.1 |
| Comparative compound | 15.2 |

It is clear from Table 4 mentioned above that the compounds No. 5, No. 41 and No. 42, which are represented by Formula (I) mentioned above, have low sublimability.

Evaluation Examples 2-1 to 2-4 and Comparative Evaluation Example 2-1

Evaluation of Sensitivity to I Line

The sensitivity to radiation of the obtained radically polymerizable compositions No. 1 to No. 4 and comparative radically polymerizable composition No. 1 was evaluated as follows.

That is, the radically polymerizable composition was applied to a glass substrate by spin-coating, prebaked at 90° C. for 90 seconds using a hot plate, and exposed via a mask using a high-pressure mercury lamp provided with an i line band pass filter as a light source. The composition was developed using a 2.5 mass % aqueous solution of sodium carbonate as a developing solution, and then washed well using water. Postbaking was performed at 230° C. for 30 minutes using an oven, and thus a pattern was fixed. The pattern was observed under an electron microscope, and the minimum exposure value at which the pattern with a 20-μm opening remained was taken as sensitivity to i line. It should be noted that the exposure value of less than 200 mJ/cm² was evaluated as "A", the exposure value of 200 to 500 mJ/cm² was evaluated as "B", and the exposure value of more than 500 mJ/cm² was evaluated as "C". Table 5 shows the test results.

TABLE 5

| Radically polymerizable composition | Sensitivity to i line |
|---|---|
| No. 1 (Example 2-1) | A |
| No. 2 (Example 2-2) | A |
| No. 3 (Example 2-3) | A |
| No. 4 (Example 2-4) | A |
| Comparative No. 1 (Comparative Example 2-1) | B |

It is clear from Table 5 mentioned above that the compounds represented by Formula (I) mentioned above have better sensitivity to near-ultraviolet light such as i line than that of the comparative compound.

Therefore, the compounds represented by Formula (I) mentioned above are useful as a polymerization initiator because the sensitivity is maintained and the sublimability is low.

INDUSTRIAL APPLICABILITY

The α-aminoalkylphenone compound according to the present invention has good stability and low sublimability, efficiently generates radicals when irradiated with a bright line at 365 nm (i line) or the like, and is useful as a polymerization initiator to be used in a radically polymerizable composition.

The invention claimed is:

1. An α-aminoalkylphenone compound comprising one of the following formulas:

Compound No. 5

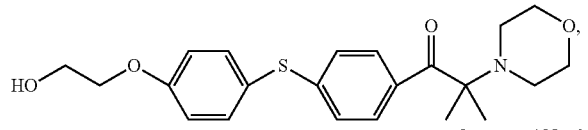

Compound No. 8

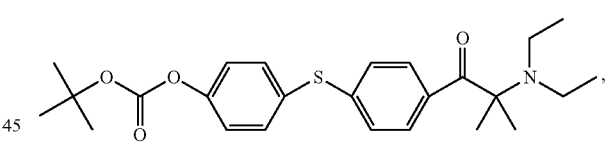

Compound No. 41

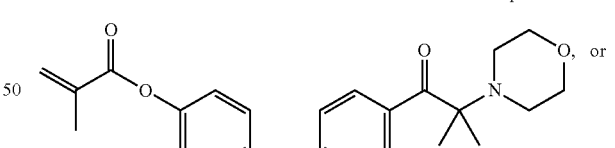

Compound No. 42

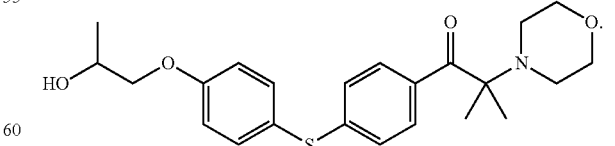

2. A polymerization initiator comprising the α-aminoalkylphenone compound according to claim 1.

3. A radically polymerizable composition comprising a polymerization initiator (A) and a polymerizable compound having an ethylenically unsaturated bond (B), wherein the polymerization initiator (A) is the polymerization initiator according to claim 2.

4. A cured product obtained by irradiating the radically polymerizable composition according to claim 3 with an energy beam.

5. A method for producing a cured product, comprising:
irradiating the radically polymerizable composition according to claim 3 with an energy beam.

* * * * *